(12) United States Patent
Filipe Pinto Silva

(10) Patent No.: US 9,983,193 B2
(45) Date of Patent: *May 29, 2018

(54) POSITIONING MECHANISM

(71) Applicant: BIOSURFIT S.A., Aveiro (PT)

(72) Inventor: Tiago Filipe Pinto Silva, Lisbon (PT)

(73) Assignee: Biosurfit, S.A., Aveiro (PT)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/631,356

(22) Filed: Jun. 23, 2017

(65) Prior Publication Data

US 2017/0284998 A1 Oct. 5, 2017

Related U.S. Application Data

(63) Continuation of application No. 15/515,511, filed as application No. PCT/EP2015/072387 on Sep. 29, 2015.

(51) Int. Cl.
*G01N 21/00* (2006.01)
*G01N 33/49* (2006.01)
(Continued)

(52) U.S. Cl.
CPC .......... *G01N 33/49* (2013.01); *B01L 3/50273* (2013.01); *B01L 3/502715* (2013.01);
(Continued)

(58) Field of Classification Search
CPC .. G01N 33/49; G01N 21/07; B01L 3/502715; B01L 3/50273; B01L 2200/025;
(Continued)

(56) References Cited

U.S. PATENT DOCUMENTS 5,129,803 A * 7/1992 Nomura ................. E01C 19/00
404/102
2005/0116530 A1* 6/2005 Simpson ................. B60B 7/20
301/37.25
(Continued)

FOREIGN PATENT DOCUMENTS

EP 1420250 A1 5/2004
EP 2 684 606 A1 1/2014
(Continued)

OTHER PUBLICATIONS

PCT International Search Report and Written Opinion for PCT/EP2015/072387, dated Nov. 19, 2015, 10 pgs.
(Continued)

*Primary Examiner* — Hina F Ayub
(74) *Attorney, Agent, or Firm* — Patterson Thuente Pedersen, P.A.

(57) ABSTRACT

A drive system for aligning a detection zone of a cartridge with an image capture device is provided. The drive system can include a first motor configured for the purpose of spinning the cartridge to drive centrifugal flow of a liquid in the cartridge. The drive system can further include a second motor coupled to a cartridge-aligning member, configured for the purpose of aligning the detection zone with the image capture device. Advantageously, each motor can be adapted for its specific purpose.

21 Claims, 2 Drawing Sheets

(51) Int. Cl.
  *B01L 3/00* (2006.01)
  *G01B 11/26* (2006.01)
  *G01N 21/07* (2006.01)

(52) U.S. Cl.
  CPC .............. *G01B 11/26* (2013.01); *G01N 21/07* (2013.01); *B01L 2200/025* (2013.01); *B01L 2200/143* (2013.01); *B01L 2300/0803* (2013.01); *B01L 2400/0409* (2013.01)

(58) Field of Classification Search
  CPC ....... B01L 2200/143; B01L 2300/0803; B01L 2400/0409; G01B 11/26
  USPC .......................................................... 356/72
  See application file for complete search history.

(56) References Cited

U.S. PATENT DOCUMENTS

| | | | |
|---|---|---|---|
| 2006/0091085 A1* | 5/2006 | Kobayashi | B01L 3/50273 210/787 |
| 2008/0058991 A1 | 3/2008 | Lee et al. | |
| 2010/0254238 A1 | 10/2010 | Kim et al. | |
| 2010/0312574 A1† | 12/2010 | Yoo | |
| 2012/0024083 A1* | 2/2012 | Wo | B01L 3/502738 73/863.21 |
| 2014/0017811 A1 | 1/2014 | Bae | |
| 2014/0072474 A1* | 3/2014 | Kido | B01F 11/0074 422/82.09 |
| 2017/0216843 A1* | 8/2017 | Filipe Pinto Silva | B01L 3/502715 356/39 |

FOREIGN PATENT DOCUMENTS

| | | |
|---|---|---|
| EP | 2 698 639 A1 | 2/2014 |
| WO | WO 2006/023563 A2 | 3/2006 |
| WO | WO 2013/135713 A1 | 9/2013 |

OTHER PUBLICATIONS

Third Party Observation for Application No. EP 20150771105, dated Dec. 18, 2017, 5 pages.

\* cited by examiner
† cited by third party

POSITIONING MECHANISM

RELATED APPLICATIONS

This application is a continuation of application Ser. No. 15/515,511 filed Mar. 29, 2017, which is a National Phase entry of PCT Application No. PCT/EP2015/072387, filed Sep. 29, 2015, which claims priority from Great Britain Application No. 1417184.7, filed Sep. 29, 2014, and which claims priority from Portuguese Application No. 107929 W, filed Sep. 29, 2014, the disclosures of which are hereby incorporated by referenced herein in their entirety.

FIELD OF THE INVENTION

The present invention relates to systems and methods for aligning a detection zone of a cartridge with an image capture device, in particular, although not exclusively, for the purpose of imaging a liquid sample in the detection zone.

BACKGROUND OF THE INVENTION

The analysis of liquid samples, more specifically blood samples, is frequently carried out in the diagnosis of various medical conditions. In particular, processing a sample on a microfluidic liquid handling structure, for example provided on a cartridge, is a widely-used technique. Such processing may include centrifugally driving liquid flow within the cartridge by rotating it.

Processing a blood sample may also include imaging the sample and the cells contained within it. Imaging the sample in this way can be used to count blood cells and the number of different types of blood cell. Generally, only a drop of blood is used in the processing and the dimensions of the microfluidic liquid handling structures of the cartridge are of the order of micrometers. For example, a detection zone in which a blood sample is held during the imaging may be 500 µm across. In order to take images of a sample when it is in such a detection zone, the detection zone must be aligned with an image capture device. The field of view of the image capture device may typically be 200 µm across and to align the detection zone and the field of view of the image capture device, a sufficient degree of accuracy in angularly positioning the detection zone of the cartridge relative to the image capture device is required.

As mentioned above, processing a blood sample may also involve centrifugally driving liquid flow within the cartridge by rotating the cartridge. To centrifugally drive liquid flow, the cartridge must be rotated at frequencies higher than those that would generally be used to position a cartridge relative to an image capture device. To rotate the cartridge at these higher frequencies, a motor such as those typically used to spin a disc in a DVD or CD drive, such as a brushless DC (BLDC) motor, may be used. An advantage of using this type of motor is that such motors are widely available and inexpensive, compared to more specialised motors often used in laboratory experiments. However, whilst such motors are suitable for rotation at frequencies required to centrifugally drive liquid flow, they do not have sufficient accuracy, in terms of angular positioning of the cartridge, to align a detection zone of a cartridge, which may be 500 µm across, with an image capture device with a field of view that may be 200 µm across. A typical motor such as those typically used to spin a disc in a DVD or CD drive, for example a brushless DC motor, is not sufficiently accurate for the purposes of aligning a detection zone and an image capture device such as those described above. Motors may be available which would be capable of both rotating the cartridge at frequencies sufficiently high in order to centrifugally drive liquid flow in the cartridge and aligning the detection zone with the image capture device, but such motors are likely to be more expensive than motors such as those used in DVD or CD drives.

It would be desirable for a drive system for an analytic cartridge to be able to accurately position the cartridge and drive it at a sufficient speed in a way that affords significant design freedom and flexibility and/or in a cost efficient manner.

SUMMARY OF THE INVENTION

Aspects of the invention are set out in the independent claims. Further, optional features of embodiments of the invention are set out in the dependent claims.

In some embodiments there is provided a drive system for spinning a liquid handling cartridge and aligning a detection zone of the cartridge with an image capture device. The drive system comprises a cartridge-securing member which is configured to securely engage a feature of the cartridge to enable rotation of the cartridge about an axis of rotation. The drive system further comprises a first motor which is coupled to the cartridge-securing member to drive rotation of the cartridge when the cartridge is engaged with the cartridge-securing member. The drive system further comprises a cartridge-aligning member, which has a first configuration in which movement of the cartridge-aligning member causes rotation of the cartridge about the axis of rotation, when the cartridge is engaged with the cartridge-securing member. The cartridge-aligning member also has a second configuration in which the cartridge, when engaged with the cartridge-securing member, is free to rotate about the axis, independent of movement of the cartridge-aligning member. The drive system further comprises a second motor which is coupled to the cartridge-aligning member to drive the cartridge-aligning member to align the detection zone of the cartridge with the image capture device. In some embodiments, one or both of the first and second motors may be stepper motors and in some embodiments, the first motor may be a motor of the type used in DVD or CD drives, for example a brushless DC (BLDC) motor.

Advantageously, using a respective motor for each of the tasks of spinning and aligning affords greater flexibility in the design and choice of motors and related components. Moreover, a combination of higher speed and accuracy than may be possible with a single motor may be achieved.

In some embodiments, the maximum precision of the second motor and cartridge-aligning member for angularly positioning the cartridge is better than the maximum precision of the first motor and cartridge-securing member for angularly positioning the cartridge. Advantageously, by using two separate motors, speed and accuracy can be combined in a cost-efficient manner. The first motor is capable of driving rotation of the cartridge at higher frequencies than the second motor. The second motor has better accuracy than the first motor in terms of angular positioning of the cartridge relative to the image capture device but may not be capable of driving rotation of the cartridge at sufficiently high frequencies, in contrast to the first motor. Using two separate motors which are each configured for one of the two tasks may afford cost savings relative to a single motor which is configured for both tasks.

In some embodiments, the cartridge-aligning member comprises a wheel. In more specific embodiments, the wheel may be shaped as follows:

over a first portion of its angular extent, the perimeter of the wheel is substantially circular, and over a second portion of its angular extent, the wheel has a radial extent less than that of the first portion.

Advantageously, the smaller radial extent over the second portion of the wheel's angular extent means that when the second portion is facing a surface that rotates about the axis of rotation with the cartridge, for example the cartridge itself, the wheel is not in contact with that surface and the cartridge may rotate freely, independent of movement of the wheel. In this orientation, the wheel is in the second configuration described above. Conversely, when the first portion of the wheel's angular extent is facing the surface, the wheel is in contact with the surface. In this orientation, the wheel is in the first configuration, i.e. the configuration in which rotation of the wheel causes rotation of the cartridge. The wheel is thus in the first configuration, as described above, in a first orientation and in the second configuration in a second orientation and can transition between the configurations by rotating.

Another way of describing the specific shape of the wheel described above is that a cross-section of the wheel in the plane of the wheel substantially forms a circle, wherein for a subset of the radially outermost points of the cross-section, the distances between each of the subset of points and the centre of the circle are each less than the radius of the circle. The smaller radial extent of the wheel over the second portion of its angular extent may be achieved by removing an outer portion of a circular or substantially circular wheel. In specific embodiments, the perimeter of the wheel over the second portion of the wheel's angular extent may be a straight line, perpendicular to a radius of the wheel. In other embodiments, the perimeter of the wheel over the second portion of the wheel's angular extent may be curved.

In some embodiments, the wheel has a resilient surface along at least a portion of its perimeter. In more specific embodiments, this portion of the perimeter of the wheel along which the wheel has a resilient surface includes the perimeter of the wheel over the first portion of its angular extent.

In some embodiments, the cartridge-aligning member is configured to align the detection zone of the cartridge by rotation of the wheel. Depending on the amount of rotation of the cartridge that is required to align the detection zone and the image capture device, the wheel may be driven to rotate over one or more turns. Because of the shape of the wheel, as described above, if the wheel is rotated multiple times, the cartridge will not be rotated in one smooth movement, however rotation of the cartridge in one smooth movement is not necessarily required.

Advantageously, the size of the wheel, more specifically the diameter of the wheel, can be selected to control the balance between the accuracy in terms of angular positioning of the wheel and the speed with which rotation of the cartridge can be driven by the second motor. For example, one complete rotation of a small wheel will rotate the cartridge by a small amount relative to one complete rotation of a larger wheel. One rotation of the rotor of the second motor thus translates into a smaller amount of rotation of the cartridge when a small wheel is employed than when a larger wheel is employed. However, rotating the cartridge by a fixed amount using the same motor would take a longer time with a smaller wheel than with a larger wheel.

In some embodiments, the cartridge-aligning member is configured to transition between the first and second configurations by rotation of the wheel, as mentioned above. Transitioning between the first and second configurations by rotation of the wheel is advantageous because the wheel is configured to rotate in any case, in order to drive rotation of the cartridge. No additional moving parts are therefore required to facilitate the transition of the cartridge-aligning member between the first and second configurations.

In some embodiments, the cartridge-aligning member, for example a wheel, is configured to transition between the first and second configurations by linear movement of the wheel or, for example, by tilting about a point, for example tilting an axis of rotation of the wheel. This may involve moving only the wheel or moving an assembly which comprises both the wheel and the second motor.

In some embodiments, the drive system further comprises sensor and, in some embodiments, a home feature on the wheel. This home feature is detected by the sensor when the wheel is in the second configuration. In some embodiments, the home feature comprises a hole in the wheel.

In some embodiments, rather than a wheel, the cartridge-aligning member may comprise a finger of material, such as rubber, which is configured for engagement with the cartridge and which, in the first configuration, is in contact with the cartridge. In the first configuration, rotation of the finger about the axis of rotation of the cartridge drives rotation of the cartridge about the same axis. In moving between the first and second configurations, the finger may be moved linearly such that the finger is no longer in contact with the cartridge. This movement may involve moving an assembly comprising both the finger and the second motor or just the finger.

In some embodiments, the cartridge-aligning member, in the first configuration, is in contact with the cartridge. In embodiments where the cartridge-aligning member comprises a wheel, the wheel may be in contact with the cartridge.

In some embodiments, the wheel is configured to enhance frictional engagement of the wheel with the cartridge. For example, the wheel may be comprised of rubber or another suitable material.

In some embodiments, the cartridge has a substantially planar surface and the aligning member, in the first configuration, when the cartridge is secured by the cartridge-securing member, is in contact with the substantially planar surface to align the detection zone of the cartridge with the image capture device. Alternatively, in some embodiments, the aligning member, in the first configuration, when the cartridge is secured by the cartridge-securing member, may be in contact with a surface of the cartridge which is substantially perpendicular to the substantially planar surface of the cartridge, to align the detection zone of the cartridge with the image capture device.

In some embodiments, the cartridge is generally disc-shaped and the cartridge-aligning member, in the first configuration, when the cartridge is secured by the cartridge-securing member, is in contact with a face of the disc. Alternatively, in some embodiments in which the cartridge is generally disc-shaped, the cartridge-aligning member, in the first configuration, when the cartridge is secured by the cartridge-securing member, is in contact with an edge of the disc.

An advantage of the wheel, or a cartridge-aligning member more generally, being in contact with the cartridge itself is that in being in contact with the cartridge, the cartridge-aligning member acts as a spacer and maintains a constant distance between the image capture device and the detection zone of the cartridge.

In some embodiments, the cartridge may be circular or substantially circular and may, in other embodiments, comprise another shape. For example, the cartridge may be square or rectangular. Further, the cartridge may not necessarily be planar.

The cartridge may, in some embodiments, comprise a microfluidic device, for example a device such as that described in patent application GB1417178.9 or patent application WO2013135713, both of which are incorporated herein by reference.

In embodiments described above, the cartridge-aligning member, in the first configuration, is in contact with the cartridge. Alternatively, in some embodiments, the cartridge-aligning member, in the first configuration, may be in contact with the cartridge-securing member. For example, in embodiments where the cartridge-securing member is a spindle configured to engage with a central hole of a disc-shaped cartridge, the cartridge-aligning member, in the first configuration, may be in contact with the spindle. The cartridge-aligning member may drive rotation of the spindle which in turn drives rotation of the cartridge.

Further, in some embodiments, the cartridge-aligning member may be in contact with a rotor of the first motor. The cartridge-aligning member may drive rotation of the rotor of the first motor, which in turn drives rotation of the cartridge-engaging member, which in turn drives rotation of the cartridge. Configuring the drive system such that in the first configuration, the cartridge-aligning member is in contact with a part of the system other than the cartridge itself may be advantageous in embodiments where the cartridge does not have a portion which is planar over its full angular extent or at least a portion of its angular extent. In embodiments in which the cartridge-aligning member, in the first configuration, is in contact with the cartridge, this portion of the cartridge which is planar over the full angular extent of the cartridge would be required so that the surface of the cartridge is a constant distance from the centre of the wheel through a full rotation of the cartridge about the axis of rotation.

As mentioned above, in some embodiments, the cartridge-securing member may comprise a spindle. In such embodiments, the cartridge may comprise a central hole configured to engage with the spindle. In some embodiments, the cartridge-securing member may comprise a turntable on which, in operation of the drive system, the cartridge is secured.

In some embodiments, the drive system may comprise a processor configured to NCScontrol the first and second motors to align the detection zone of the cartridge with an image capture device and control the image capture device to capture images. Specifically, the processor is configured to control the second motor to align the detection zone of the cartridge with the image capture device by rotating the cartridge at one or more rotational frequencies not exceeding a limit frequency. Once aligned, the processor causes the image capture device to capture images once the detection zone is aligned with the image capture device. Subsequent to capturing images, the processor causes the cartridge-alignment member to transition from the first to the second configuration to free the cartridge for rotation by the first motor. Subsequently, the processor controls the first motor to spin the cartridge to centrifugally drive liquid flow in the cartridge at a rotational frequency exceeding the limit frequency.

In some embodiments, the processor is configured to control the first motor to align the detection zone with the image capture device to within the angular precision of the first motor by rotating the cartridge at one or more rotational frequencies which do not exceed the limit frequency, before controlling the second motor to align the detection zone with the image capture device. In this way, rough alignment to within the angular precision of the first motor is followed by accurate alignment using the second motor. Alternatively, the detection zone and the image capture device may be aligned by the cartridge-aligning member and the second motor alone or may be roughly aligned manually before being aligned by the cartridge-aligning member and the second motor.

In some embodiments, the drive system may comprise a marker and the cartridge may comprise a corresponding marker. In operation of the drive system, when the cartridge is inserted into the drive system by a user, the user may align the marker on the drive system with the marker on the cartridge in order to position the detection zone of the cartridge roughly in alignment with the image capture device.

BRIEF DESCRIPTION OF THE FIGURES

Embodiments are now described in detail by way of example, with reference to the accompanying drawings, in which.

DETAILED DESCRIPTION OF THE INVENTION

Figure 1A:
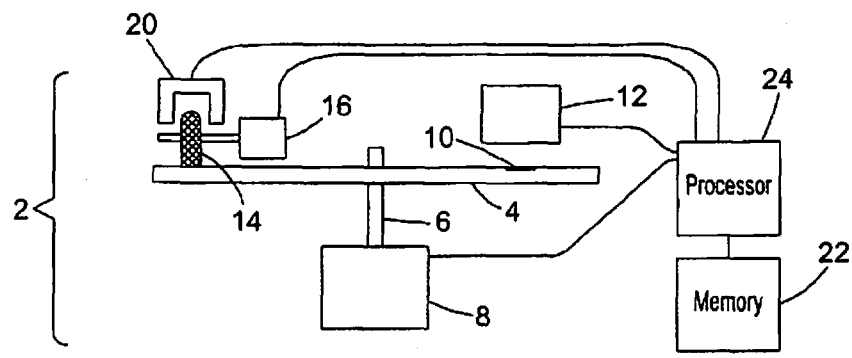
FIG. 1a illustrates a schematic side elevation of a drive system in a first configuration, together with a cartridge and an image capture device.

With reference to FIG. 1a, a drive system 2 is configured to receive a disc-shaped cartridge 4 which is itself configured to receive a liquid sample, more particularly a blood sample. The drive system 2 comprises a spindle 6, configured to engage with a central hole of the cartridge 4. Coupled to the spindle 6 is a first motor 8, which is of the type of motor that is typically used in a DVD or CD drive, for example a BLDC motor. The cartridge 4 comprises a detection zone 10 in which, in operation of the drive system 2, the blood sample is imaged. An image capture device 12 is disposed so as to be able to image the detection zone 10 and more specifically, the blood sample. In a specific example, the detection zone 10 is 500 µm across and the field of view of the image capture device 12 is 200 µm across. The drive system further comprises a wheel 14 and a second motor 16 coupled to the wheel 14. The wheel 14 is configured so as to have an axis of rotation aligned with a radius though the axis defined by the spindle 6. The wheel 14 comprises a hole 18. A sensor 20 is disposed relative to the wheel 14 to detect when the wheel 14 is in a home orientation. The sensor 20 comprises a light barrier that is interrupted by the wheel 14 unless the hole 18 is aligned with the light barrier when the wheel is in the home orientation. The drive system 2 further comprises a memory 22 associated with a processor 24 which is coupled to the image capture device 12 to receive image data for processing, to the first and second motors 8, 16 and to the sensor 20. The processor 24 is configured to control the first 8 and second 16 motors, the image capture device 12 and the sensor 20.

The wheel 14 has a first configuration and a second configuration. FIG. 1a illustrates the wheel 14 in the first configuration. In this first configuration, the wheel 14 is in contact with a face of the cartridge 4, such that rotation of the wheel 14 drives rotation of the cartridge 4.

An advantage of the wheel 14 being in contact with a face of the cartridge 4 is that the detection zone 6 of the cartridge 4 will not be less than a distance away from the image capture device 12 equal to the greatest radial extent of the wheel 14, relative to the axis of rotation of the wheel.

This effect is beneficial in terms of focusing the image capture device 12 on the sample in the detection zone 10, especially if the image capture device 12 has a short focal range, which is generally the case for the types of image capture device which are typically used in imaging blood samples contained in a microfluidic liquid handling structure. In a specific example, an assembly comprising a camera and a lens with autofocus may be used. Any digital camera may be used. As an example, a CCD global shutter digital camera may be used, for example a Point Grey Chameleon camera.

Figure 1B:
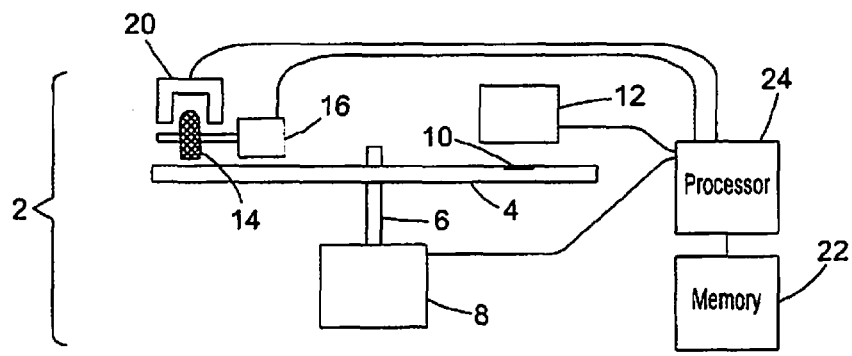
FIG. 1b illustrates the schematic side elevation of FIG. 1a with the drive system in a second configuration.

With reference to FIG. 1b, the wheel 14, in the second configuration, is not in contact with the cartridge 4. This means that when the wheel 14 is in this second configuration, the cartridge 4 is able to rotate freely, independent of movement of the wheel 14 when the motor 8 drives rotation of the cartridge 4 to centrifugally drive liquid flow in the cartridge 4. In some embodiments, the hole 18 is positioned on the wheel so that this corresponds to the home orientation, thereby enabling positive confirmation that the cartridge is free to rotate by means of the sensor 20.

Figure 1C:
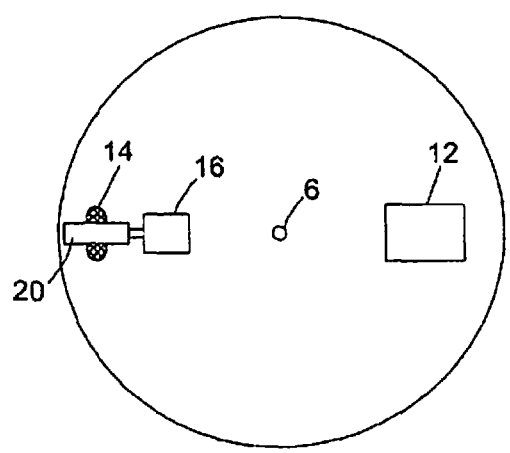
FIG. 1c illustrates schematically, from above, parts of the drive system relative to the cartridge and image capture device.

FIGS. 1a-c schematically illustrate elements of the drive system 2 involved in, in some embodiments, aligning the detection zone 10 of the cartridge 4 with the image capture device 12. Specific features commonly found in CD- or DVD-like drives are omitted for the sake of clarity of illustration, for example a drive housing, mountings for holding the elements of the drive system 2 relative to each other, a loading mechanism for loading the cartridge 4 into the drive system 2, for example a sliding tray such as those which are often employed in DVD drives and the details of how the cartridges are ordered for rotation. These standard aspects are omitted from the figures for clarity.

Figure 2:
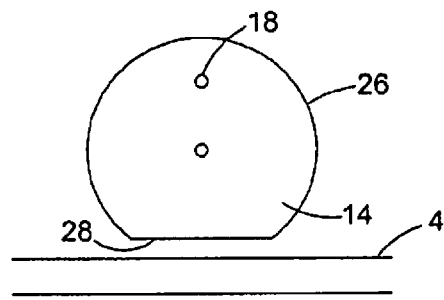
FIG. 2 illustrates a shape of a wheel for angularly positioning the cartridge relative to the image capture device.

With reference to FIG. 2, the shape of the wheel, in accordance with some embodiments, is now described. The wheel 14 substantially takes the shape of a cylinder with two circular faces, with a radius greater than the height of the cylinder. Regarding the perimeter of the wheel 14, the perimeter of the wheel 14 is substantially circular over a first portion 26 of its angular extent. Over a second portion 28 of its angular extent the wheel has a radial extent less than that of the first portion 26. This shape can be notionally (or even actually) achieved by starting with a cylindrical wheel, with two circular faces and removing an outer portion of the wheel. The cross-section of such an outer portion in the plane of the wheel may be, for example, a minor segment of a circle. In some specific embodiments, the hole 18 is located opposite the second portion 28 of the wheel's angular extent between the central hole of the wheel 14 and the wheel's perimeter.

Figure 3:
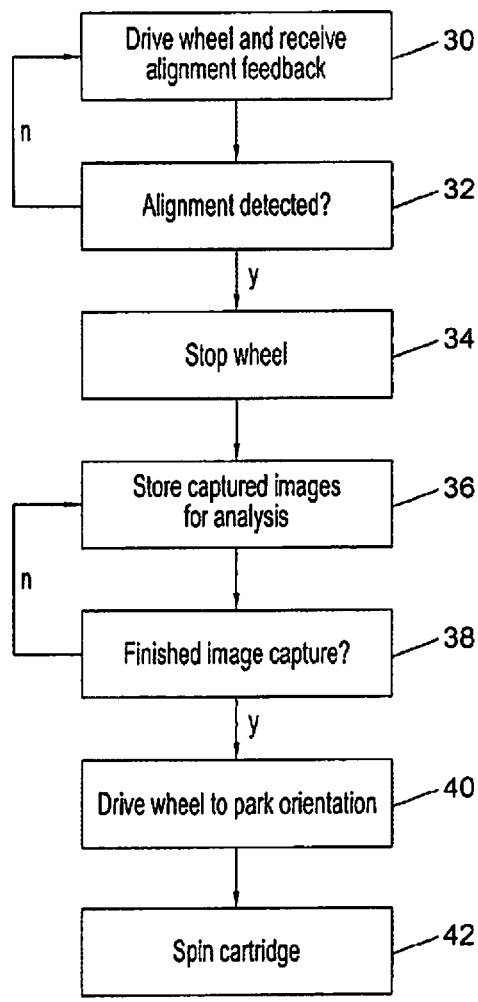
FIG. 3 illustrates a flow diagram representing a method of operating the drive system.

With reference to FIG. 3, the steps carried out by the processor 24 in operation of the drive system 2 are now described, starting from the point at which the cartridge 4 comprising a sample that flows through the cartridge by way of capillary effect has been loaded into the drive system 2. Initially, the wheel 14 is in the second configuration, i.e. it is disengaged from the cartridge 4, in some embodiments in the home orientation as indicated by a signal from the sensor 20, although the disengaged orientation can equally be defined by an offset relative to the home position.

At step 30, the processor 24 sends a signal to the second motor 16, to cause it to drive rotation of the wheel 14 in order to align the detection zone 10 with the field of view of the image capture device 12. In some embodiments, the motor 16 is a stepper motor and the signal is in the form of one or more steps relative to the home orientation. The processor 24 also sends a signal to the image capture device 12 to cause it to start capturing images. The images are sent back to the processor 24 as feedback on the alignment. The processor 24 determines the value of one or more image parameters of each image and stores it in the memory 22 associated with the processor 24.

At step 32, the processor 24 checks if alignment has been achieved by evaluating an alignment condition. For example, the processor 24 monitors the values of the image parameter for a significant change in the values or for certain parameter values indicative of alignment. During alignment, different parameters of the image can be monitored, depending on what is expected to be found in the region of interest. These parameters may be: light intensity, color, contrast, specific patterns, etc. If the check indicates no alignment, the processor 24 loops back to step 30 to continue driving the wheel 14 to bring the detection zone 10 in alignment with the field of view of the image capture device 12. If the alignment condition indicates that the detection zone 10 and the field of view of the image capture device 12 are aligned, the processor 24, at step 34, ceases to send further drive signals to the second motor 16, stopping rotation of the wheel 14, as the detection zone 10 is now aligned with the field of view of the image capture device 12. The wheel 14 and the cartridge thus cease to rotate.

At step 36, the processor 24 begins to store images received from the image capture device in the memory 22, for example for the purposes of determining a blood count, in case of the sample being a blood sample. In some embodiments, the processor 24 stores and analyses the images as they are received from the image capture device 12.

Step 36, in some embodiments, includes a wait loop to ensure a predetermined amount of time has passed since the cartridge was loaded to ensure the sample has arrived in the detection zone 10, or the arrival of the sample may be confirmed by image processing.

The images may be captured for a predetermined period of time, for example one or more minutes and stored in the memory 22. At step 38, the processor 24 continuously carries out a check as to whether the predetermined period of time is over (or whether a stopping condition is met). If the stopping condition is not met, the process loops back to step 36. When the processor 24 determines that the stopping condition is met, at step 40, the processor 24 sends a signal to the second motor 16 to cause it to drive rotation of the wheel 14 to a park orientation where the cartridge is free to rotate. For example, in some embodiments, when the sensor 20 detects hole 18 in the wheel 14, the wheel 14 is in the second configuration, i.e. disengaged from the cartridge 4, and the sensor 20 sends a signal to the processor 24. In turn, the processor 24 ceases to send signals to the second motor 16 to cause it to stop driving rotation of the wheel 14 further.

At step 42, with the wheel 14 disengaged from the cartridge 4, the processor 24 sends a signal to the first motor 8, to cause it to drive rotation of the cartridge 4, at a higher rate of rotation than used for alignment, typically to drive centrifugal liquid flow inside the cartridge, for other types of sample processing.

FURTHER EMBODIMENTS

In the specific embodiments described above, the drive system is configured to receive a disc-shaped cartridge. It will be appreciated that the drive system can also be configured to receive cartridges of other shapes. Further, the cartridge may not necessarily be planar.

Similarly, the wheel in the specific embodiments described above substantially forms the shape of a cylinder with circular faces. The wheel may also have rounded edges, such that the intersection between the face of the cylinder and the edge of the cylinder does not form a right angle but instead consists of a more gradual transition.

In the specific embodiments described above, the processor monitors a parameter of the captured images, for example the light intensity, and evaluates an alignment condition. The monitored image parameter may equally be colour or contrast. The processor may also, in some embodiments, detect alignment of the image capture device and the detection zone by recognising specific patterns.

In the specific embodiments described above, the processor causes the image capture device to begin storing images in the memory associated with the processor and causes the image capture device to stop capturing images after a predetermined period of time. Equally, rather than capturing images for a predetermined period of time, a preset number of images may be taken. Equally, a preset number of images may be stored in the memory associated with the processor, after which the processor sends a signal to the image capture device to cause it to stop capturing images. Images may be captured throughout and only the storage of images used for sample analysis implemented.

The above description of embodiments is made by way of example only and various modifications, alterations and juxtapositions of the described features will occur to the person skilled in the art. It will therefore be apparent that the above description is made for the purpose of illustration of embodiments of the invention and not limitation of the invention, which is defined in the appendant claims.

The invention claimed is:

1. A drive system for spinning a liquid handling cartridge and aligning a detection zone of the cartridge with an image capture device, the drive system comprising:
    a cartridge-securing member being configured to securely engage a feature of the cartridge to enable rotation of the cartridge about an axis of rotation;
    a first motor coupled to the cartridge-securing member to drive rotation of the cartridge when the cartridge is engaged with the cartridge-securing member;
    a cartridge-aligning member configurable in a first configuration such that movement of the cartridge-aligning member causes rotation of the cartridge about the axis, when the cartridge is engaged with the cartridge-securing member, and in a second configuration such that the cartridge, when engaged with the cartridge-securing member, is free to rotate about the axis independent of movement of the cartridge-aligning member; and
    a second motor coupled to the cartridge-aligning member to drive the cartridge-aligning member to align the detection zone of the cartridge and the image capture device.

2. A system as claimed in claim 1, wherein the first motor and cartridge-securing member are capable of rotating the cartridge faster than the second motor and cartridge-aligning member and the second motor and cartridge-aligning member are capable of angularly positioning the cartridge with a better precision than the first motor and cartridge-securing member.

3. A system as claimed in claim 1, wherein the cartridge-aligning member comprises a wheel.

4. A system as claimed in claim 3, wherein a perimeter of the wheel is substantially circular over a first portion of its angular extent and the wheel has a radial extent less than a radial extent of the first portion over a second portion of its angular extent, the first portion facing the cartridge in the first configuration and the second portion facing the cartridge in the second configuration.

5. A system as claimed in claim 3, wherein the wheel is in a first orientation in the first configuration and in a second orientation in the second configuration.

6. A system as claimed in claim 3, the wheel having a resilient surface along at least a portion of its perimeter.

7. A system as claimed in claim 3, wherein the wheel is configured for engagement of the cartridge.

8. A system as claimed in claim 3, wherein the cartridge-aligning member is configured to align the detection zone of the cartridge by rotation of the wheel.

9. A system as claimed in claim 8, wherein the cartridge-aligning member is configured to transition between the first and the second configuration by rotation of the wheel.

10. A system as claimed in claim 3, wherein the system further comprises a home feature on the wheel and a sensor for detecting the home feature, thereby to detect the wheel being disposed in a home orientation.

11. A system as claimed in claim 1, wherein the cartridge has a substantially planar surface and the aligning member, in the first configuration, when the cartridge is secured by the cartridge-securing member, is in contact with the substantially planar surface to align the detection zone of the cartridge with the image capture device.

12. A system as claimed in claim 1, wherein the cartridge is generally disc-shaped and the aligning member, in the first configuration, when the cartridge is secured by the cartridge-securing member, is in contact with a face of the disc.

13. A system as claimed in claim 1, the system comprising a processor configured to
    control the second motor to align the detection zone with the image capture device by rotating the cartridge at one or more rotational frequencies not exceeding a limit frequency;
    receive one or more images from the image capture device while the detection zone and the image capture device are aligned;
    subsequent to receiving the one or more images while the detection zone and the image capture device are aligned, cause the second motor to transition the cartridge-alignment member from the first to the second configuration to free the cartridge for rotation by the first motor; and
    subsequent to freeing the cartridge for rotation by the first motor, control the first motor to spin the cartridge to centrifugally drive liquid flow in the cartridge at a rotational frequency exceeding the limit frequency.

14. A system as claimed in claim 1, wherein the liquid handling cartridge is a microfluidic device.

15. A method of aligning a detection zone on a liquid handling cartridge with an image capture device, wherein the cartridge is secured to a first member defining an axis of rotation for the cartridge, the method comprising:
- engaging the cartridge with a second member;
- driving the second member to align a detection zone on the cartridge with the image capture device by rotating the cartridge at one or more rotational frequencies below a limit frequency to substantially avoid centrifugally driven liquid flow in the cartridge;
- receiving images from the image capture device while the detection zone is aligned with the image capture device;
- disengaging the second member from the cartridge; and
- driving the first member to spin the cartridge at one or more rotational frequencies exceeding the limit frequency to centrifugally drive liquid flow in the cartridge.

16. A drive system for spinning a liquid handling cartridge and aligning a detection zone of the cartridge with an image capture device, the drive system comprising:
- a cartridge-securing member being configured to securely engage a feature of the cartridge to enable rotation of the cartridge about an axis of rotation;
- a first motor coupled to the cartridge-securing member to drive rotation of the cartridge when the cartridge is engaged with the cartridge-securing member;
- a wheel configurable in a first configuration such that movement of the wheel causes rotation of the cartridge about the axis, when the cartridge is engaged with the cartridge-securing member, and in a second configuration such that the cartridge, when engaged with the cartridge-securing member, is free to rotate about the axis independent of movement of the wheel; and
- a second motor coupled to the wheel to drive the wheel to align the detection zone of the cartridge and the image capture device.

17. A system as claimed in claim 16, wherein the first motor and cartridge-securing member are capable of rotating the cartridge faster than the second motor and wheel and the second motor and wheel are capable of angularly positioning the cartridge with a better precision than the first motor and cartridge-securing member.

18. A system as claimed in claim 16, wherein the cartridge has a substantially planar surface and the wheel, in the first configuration, when the cartridge is secured by the cartridge-securing member, is in contact with the substantially planar surface to align the detection zone of the cartridge with the image capture device.

19. A system as claimed in claim 16, wherein the cartridge is generally disc-shaped and the wheel, in the first configuration, when the cartridge is secured by the cartridge-securing member, is in contact with a face of the disc.

20. A system as claimed in claim 16, the system comprising a processor configured to:
- control the second motor to align the detection zone with the image capture device by rotating the cartridge at one or more rotational frequencies not exceeding a limit frequency;
- receive one or more images from the image capture device while the detection zone and the image capture device are aligned;
- subsequent to receiving the one or more images while the detection zone and the image capture device are aligned, cause the second motor to transition the wheel from the first to the second configuration to free the cartridge for rotation by the first motor; and
- subsequent to freeing the cartridge for rotation by the first motor, control the first motor to spin the cartridge to centrifugally drive liquid flow in the cartridge at a rotational frequency exceeding the limit frequency.

21. A system as claimed in claim 16, wherein the liquid handling cartridge is a microfluidic device.

* * * * *